(12) United States Patent
Rodriguez-Kabana

(10) Patent No.: US 7,572,460 B2
(45) Date of Patent: Aug. 11, 2009

(54) HYDROGEN CYANAMIDE PESTICIDE FORMULATIONS

(76) Inventor: Rodrigo Rodriguez-Kabana, 1026 E. Samford Ave., Auburn, AL (US) 36830-6133

( * ) Notice: Subject to any disclaimer, the term of this patent is extended or adjusted under 35 U.S.C. 154(b) by 26 days.

(21) Appl. No.: 11/259,435

(22) Filed: Oct. 25, 2005

(65) Prior Publication Data
US 2007/0092581 A1   Apr. 26, 2007

(51) Int. Cl.
*A01N 25/02* (2006.01)
(52) U.S. Cl. .................. 424/405; 43/125; 424/40; 424/44; 504/141; 514/557; 514/609
(58) Field of Classification Search ............... None
See application file for complete search history.

(56) References Cited

U.S. PATENT DOCUMENTS

| | | |
|---|---|---|
| 4,259,344 A | 3/1981 | Gonczi et al. |
| 5,045,105 A | 9/1991 | Grossmann et al. |
| 5,084,477 A | 1/1992 | Walter et al. |
| 5,693,591 A | 12/1997 | North et al. |
| 5,726,129 A | 3/1998 | Barnes et al. |
| 5,885,932 A | 3/1999 | Parr et al. |
| 6,514,510 B1 * | 2/2003 | Fukuchi ............. 424/406 |
| 6,746,988 B2 * | 6/2004 | Hopkinson et al. ......... 504/127 |
| 6,852,341 B2 | 2/2005 | Rodriguez-Kabana |
| 6,878,389 B2 | 4/2005 | Rodriguez-Kabana |
| 6,932,985 B2 | 8/2005 | Rodriguez-Kabana |
| 2008/0171772 A1 * | 7/2008 | Beard et al. ............. 514/339 |
| 2008/0171778 A1 * | 7/2008 | Wallace et al. ............. 514/394 |

OTHER PUBLICATIONS

Williamson, J.G. et al.; "Reproductive Growth and Development of Blueberry"; 2004, *University of Florida IFAS Extension*, No. HS976, 7 pages.

"Pesticide-Related Illnesses Associated with the Use of a Plant Growth Regulator-Italy, 2001"; 2001, *The Journal of the American Medical Association*, vol. 286, No. 22, 4 pages.

"Pesticide-Related Illnesses Associated with the Use of a Plant Growth Regulator-Italy, 2001"; 2001, *Morbidity and Mortality Weekly Report*, vol. 50, No. 39, pp. 845-868.

"Alternatives to methyl bromide for soil treatment"; 1998, *MBTOC Assessment*, Chapter 4, pp. 35-95.

Daniel, P. et al.; "The Use of Chemical Agents for Wilting Forage Plants"; 1973, *Wirtschaftseigene Futter*, vol. 19, No. 4, pp. 269-281.

Daniel, P. et al.; "Über die Anwendung chemischer Mittel zum Vorwelken von Futterpflanzen"; 1973, *Wirtschaftseigene Futter*, vol. 19, No. 4, pp. 269-281.

* cited by examiner

*Primary Examiner*—Neil Levy

(57) ABSTRACT

Agricultural crops are protected from the growth of undesirable vegetation as well as nematode and insect infestations, by the application of hydrogen cyanamide in combination with a short-chain, water-soluble monocarboxylic acid, with improved pesticidal effect.

7 Claims, 7 Drawing Sheets

HYDROGEN CYANAMIDE PESTICIDE FORMULATIONS

BACKGROUND OF THE INVENTION

1. Field of the Invention

This invention resides in materials and methods for crop protection, and is particularly concerned with soil treatments to control the growth of nematodes and weeds.

2. Description of the Prior Art

The agricultural industry relies on effective control of insects, plant pathogens, nematodes, and weeds, for bountiful and healthy crops. The control of certain forms of nematodes, for example, is an important factor in ensuring crop plant viability in the initial stages of crop growth and likewise for plant productivity and life span in both annual and perennial crops. Effective nematode control is particularly important in view of the ability of nematodes to persist in soil after crop removal.

Known methods for controlling nematodes include crop rotation, fallowing, the use of nematode-resistant crops, and soil fumigation. Of these, soil fumigation is the method that is the most economically feasible and the most widely used, and methyl bromide is the most widely used soil fumigant. Methyl bromide is a highly effective broad spectrum pesticide that is use both in both pre-harvest and post-harvest fumigation. A difficulty with methyl bromide however is its volatility, which results in the release of a significant amount of the chemical to the atmosphere when applied to soil. This reduces the amount of methyl bromide available for pesticidal action in the soil and also causes depletion of the ozone layer due to the reaction of ozone with the bromine atoms that are released when the methyl bromide undergoes photo-oxidation. The high volatility of methyl bromide also limits the effectiveness of this fumigant in heavy soils.

Cyanamide, a term that is used to designate both hydrogen cyanamide and calcium cyanamide, is used in Europe as an herbicide and in various parts of the world as a plant growth regulator. The convenience of using the liquid formulation has increasingly made it the favored material, and research has shown hydrogen cyanamide to be the active ingredient of both cyanamide preparations. From its introduction in the 1950's, hydrogen cyanamide was used as a pre-emergence herbicide and a defoliant. The effectiveness of hydrogen cyanamide was attributable at least in part to the action of moist soil on plants in hydrolyzing calcium cyanamide to hydrogen cyanamide, which was not totally understood at the time. In the environment, hydrogen cyanamide decomposes to urea, followed by additional breakdown to ammoniacal forms of nitrogen and carbon dioxide. These metabolites become plant nutrients with their occurrence mediated by biological organisms and/or physical processes.

The rate at which hydrogen cyanamide formulations break down can be controlled by the incorporation of a stabilizing agent, and phosphoric acid has commonly served this purpose well. When drip irrigation was introduced in the 1960's, it was discovered that the inclusion of phosphoric acid in a hydrogen cyanamide formulation containing water with a high calcium content caused plugging of the drip emitters. A similar plugging was observed in spray systems with small diameter spray nozzles.

SUMMARY OF THE INVENTION

This invention resides in a series of discoveries involving the pesticidal use of hydrogen cyanamide. One such discovery is the enhancement of pesticidal activity by the addition of a lower alkyl monocarboxylic acid, which allows the combination of hydrogen cyanamide and the monocarboxylic acid to be characterized as a synergistic combination of active ingredients. Another discovery is the effectiveness of lower alkyl monocarboxylic acids as stabilizers of hydrogen cyanamide formulations. The monocarboxylic acids are found to be effective replacements for the previously used phosphoric acid, and stabilization of the hydrogen cyanamide formulation can be achieved without the inclusion of phosphoric acid, or with no more than trace amounts. A still further discovery is that soil fumigation and pesticide control in general can be achieved with hydrogen cyanamide without the need to cover the soil with a vapor-retaining barrier to control the volatilization of the treatment agent from the soil. Still further discoveries, objects, and advantages of the invention will be apparent from the description that follows.

DETAILED DESCRIPTION OF THE INVENTION AND PREFERRED EMBODIMENTS

Figure 1:
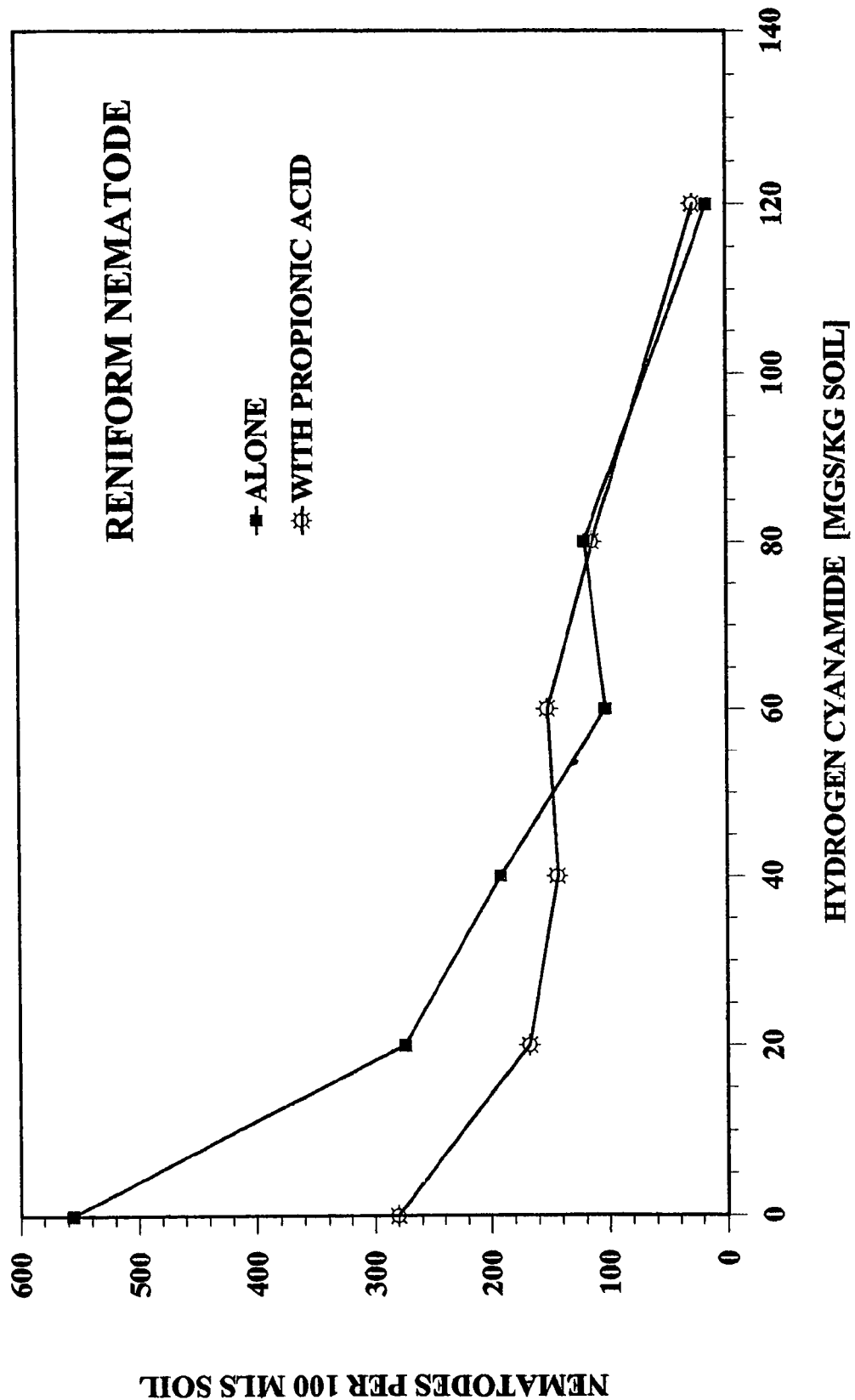
FIG. 1 is a plot of the results of tests performed in accordance with this invention, showing nematicidal activity against reniform nematodes.

The term "hydrogen cyanamide" is used herein to denote a compound of the formula

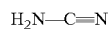

This compound is also referred to among chemists as cyanamide, cyanogenamide, and carbodiimide, and is to be distinguished from the calcium salt, calcium cyanamide

Monocarboxylic acids of use in this invention are lower-alkyl, straight-chain, water-soluble monocarboxylic acids. By "water-soluble" is meant that at least about 2 parts by weight of the acid, preferably at least about 10 parts by weight, more preferably at least about 30 parts by weight, are soluble in 100 parts by weight of water, and most preferably the acid is liquid and fully miscible with water in all proportions. Preferred monocarboxylic acids are propionic acid and butyric acid. Propionic acid is the most preferred.

The hydrogen cyanamide and the monocarboxylic acid can be applied individually to the agricultural site where pesticide control is desired, or the two chemicals can be applied together in a single application. The chemicals are most conveniently applied in aqueous solution, and can thus be applied as a common aqueous solution. Whether applied individually or in combination, the effectiveness of the two chemicals is not limited to particular weight ratios, and the weight ratios can vary widely. In most applications, however, best results will be obtained when the weight ratio of monocarboxylic acid to hydrogen cyanamide is within the range of about 1:1 to about 20:1, and preferably from about 2:1 to about 10:1. Likewise, when the chemicals are applied in aqueous solutions, the concentrations of the chemicals in the solutions are not critical and can vary widely. The most economical results will generally be achieved when the hydrogen cyanamide concentration is within the range of from about 0.1% to about 10% by weight, preferably from about 0.3% to about 3% by weight. Similarly, the most economical results with the monocarboxylic acid will be achieved when the concentration of the monocarboxylic acid is within the range of from about 0.1% to about 20% by weight, and preferably from about 1% to about 10% by weight.

Hydrogen cyanamide is commercially available and commonly prepared by the continuous carbonation of calcium cyanamide. When hydrogen cyanamide is supplied in aqueous solution, a stabilizer is typically included in the solution since the hydrogen cyanamide is susceptible to decomposition through hydrolysis. As noted above, a phosphate buffer in the form of phosphate ion or phosphoric acid is typically used as the stabilizer. In the practice of the present invention, the phosphate buffer can be retained to yield a solution containing the hydrogen cyanamide, the phosphate buffer, and the monocarboxylic acid. Alternatively, however, and preferably in many cases, the phosphate buffer can be either substantially or entirely eliminated and replaced by the monocarboxylic acid. Thus, in certain embodiments of the invention, the formulation applied to the soil or the agricultural site is an aqueous solution of hydrogen cyanamide and a monocarboxylic acid of the above description, with at most a trace amount of phosphate ion, or in certain further embodiments, a solution that is devoid of phosphate ion. The term "trace amount" is used herein to mean 1,000 ppm or less, preferably 100 ppm or less.

In the practice of this invention, the active ingredients are applied to soil or to crop growth media in general to control organisms that are considered deleterious to crop growth. These organisms include, but are not limited to, insects, nematodes, and undesired vegetation. The term "undesired vegetation" denotes non-crop plant species that otherwise tend to grow in the areas where crops are planted, and includes both volunteer crops and weeds. The undesired vegetation whose control is of greatest interest in the practice of this invention are weeds, and primarily those weeds associated with common crops such as corn, green peppers, tomatoes, soybeans, and vegetables in general, as well as cotton, sorghum, wheat, alfalfa, various ornamentals, and various turfgrasses. Nematodes that are deleterious to crop growth are plant-parasitic nematodes that include reniform nematodes (*Rotylenchulus reniformus*), spiral nematodes (*Helicotylenchus dihystera*), root-knot nematodes (*Meloidogyne arenaria, M. naasi* and *M. incognita*), stubby root nematodes (*Paratrichodorus minor*), stunt nematodes (*Tylenchorhynchus claytoni*), and others. These are distinct from nematodes that are beneficial to crop growth, examples of which are microbivorous (free-living) nematodes and other nematodes, such as those of the *Dorylaimida* order, that feed on algae, fungi, and other nematodes. The term "controlling" is used herein to denote either reducing the growth rate of the organisms, preventing the organisms from maturing, preventing the organisms from reproducing, or killing or reducing the viable population of the organisms. The term "pesticidally effective amount" is used herein to denote any amount of a treatment chemical that will produce any of these results.

In addition to the hydrogen cyanamide and the monocarboxylic acid, formulations of the present invention will optionally contain adjuvants or diluents such as formulating aids, buffers and other stabilizers, solubilizing agents, dispersing agents, crop nutrients, and other herbicides, insecticides, nematocides, or fungicides. These additives are well known in the agricultural formulations industry and readily available from suppliers of agricultural chemicals.

The types of soils in which the formulations of this invention can be effective are sandy soils, loamy soils, clays, silt, and combinations such as sandy loam, silty loam, sandy clay, and the like. When the formulations are used for controlling undesirable vegetation, effective results can be achieved with both pre-emergence application (application directly to the soil before the undesirable vegetation emerges from the soil surface) and post-emergence application (application directly to the undesirable vegetation that has already emerged). Useful methods of application include broadcast or localized spraying, drip irrigation or other forms of irrigation, and any of these methods followed by soil tilling. The application rates of the active ingredients to the soil can vary over a wide range. The optimal application rates will depend on the crop to be protected, the nature of the infestation, whether it be insect, nematode, or weed infestation, the stage of growth of the crop and of the infestation, and the manner in which application is made, i.e., whether by spraying, irrigation, or other means. For best results in controlling nematodes, the rate of application of hydrogen cyanamide will range from about 25 to about 500, and preferably from about 50 to about 250, kilograms per hectare. For best results in controlling weeds and other undesirable vegetation, the rate of application of hydrogen cyanamide will range from about 25 to about 1,000, and preferably from about 50 to about 500, kilograms per hectare. The same rates of application apply for controlling other types of infestation. The monocarboxylic acid will be applied at rates that are proportional, per the weight ratios cited above.

The compositions of this invention will generally be supplied, stored, or both, in the form of concentrates with higher proportions of the active ingredients than are contemplated for application to the growing site. These concentrates can for example be aqueous solutions containing from about 20% to about 40% each of the hydrogen cyanamide and the monocarboxylic acid. The two components can also be stored and shipped as individual aqueous concentrates.

The following examples are offered strictly for illustration and are not intended to limit the scope of the invention.

EXAMPLE 1

This example demonstrates the nematocidal activity of the combined application of hydrogen cyanamide and propionic acid to a silt loam in a covered pot, followed twelve days later by the planting of soybean seeds in the soil. In this study, the soil was naturally infested with four species of nematodes, two of which were deleterious and two beneficial, and observations were made of both the nematode survival and the growth of the soybean plants.

Stock solutions of hydrogen cyanamide at 1.0% by weight and propionic acid at 5.0% by weight, both in water, were prepared, the hydrogen cyanamide from a phosphate-buffered 50% aqueous solution. Planting pots measuring 10 cm in diameter, each containing 1 kg of soil, were used. The soil was silt loam from a cotton field, pH 6.2, CEC <10 meq/100 g soil, organic matter <1.0%. The treatment chemicals were combined in various dilutions such that 100 mL of the combined dilutions contained the desired amount of each chemical for each test. The combined dilutions were then applied to the soil surface in each pot, at 100 mL of combined dilution per pot. The dilutions were selected to achieve target application rates expressed in milligrams of the treatment chemical per kilogram of soil, with 1 milligram of treatment chemical per kilogram of soil being approximately equal to 2 kilograms of the chemical per hectare of soil or 2 pounds of the chemical per acre of soil.

Figure 2:
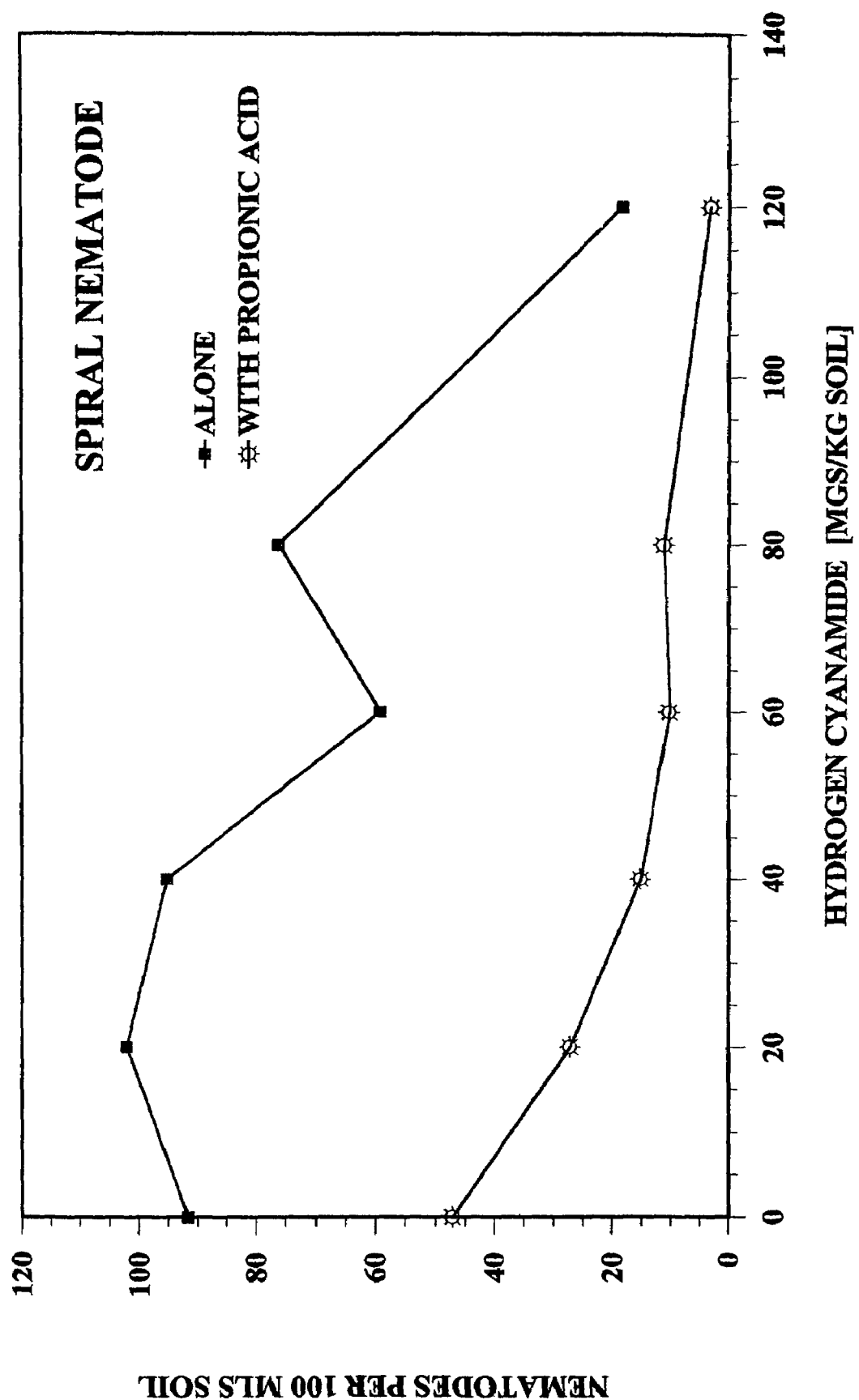
FIG. 2 is a plot of the results of tests performed in accordance with this invention, showing nematicidal activity against spiral nematodes.

Immediately after the treatment chemicals were applied, each pot was covered by a thick (1.5 mil), clear, low-density polyethylene bag. After twelve days, the bags were removed and soil samples were taken from each pot for nematological analysis by the salad bowl technique of Rodriguez-Kabana, R., and M. H. Pope, *Nematropica*, 11: 175-186 (1981). The results of these analyses are listed in Table I as pre-plant test results. The results for the two deleterious nematodes are also shown as plots of the number of nematodes vs. the hydrogen cyanamide application rate in FIGS. 1 and 2.

After the polyethylene bags were removed, each pot was planted with Hutcheson soybean seeds at 5 seeds per pot, and the seeds were allowed to germinate and the plants to grow for 45 days. The resulting plants were then removed from the pots, the root systems were washed, and the number of plants in each pot was determined. The weights of both fresh shoots and roots were also determined as well as the shoot height and the relative health of the root system, using a subjective index. Soil samples were also collected, and the soil and roots were incubated to determine nematode populations. Treatments were arranged in randomized complete block design with seven replications per treatment, and statistical evaluation of the data was performed with analyses of variance (ANOVA) and standard regression procedures. Fischer's Least Significant Difference at p 0.05 was calculated when appropriate. The results of these tests are listed as final test results in Tables II, III, and IV, with nematode populations in the soil listed in Table II, the nematode populations in the root systems in Table III, and the plant and root parameters of the soybean shoots in Table IV.

The pre-plant and final test results collectively indicate that the propionic acid significantly improved the nematicidal activity of the hydrogen cyanamide against both the reniform and spiral nematodes to a degree exceeding any additive effect of the two chemicals individually. Conversely, the populations of the microbivorous and *Dorylaimida* nematodes were either not affected or were increased by the treatments depending on the amount of cyanamide used. Regarding the conditions of the soybean plants, the treatments with cyanamide alone and with cyanamide in combination with propionic acid both resulted in increased shoot height and increased weights of the roots and the shoots, all proportional to the amount of cyanamide applied. The relative health of the root systems was also markedly improved by the treatments in a manner proportional to the dosage.

TABLE I

Nematicidal Activity of Cyanamid and Propionic Acid in Combination
Pre-Plant Test Results: 12 Days After Treatment and Prior to Crop Planting
(Cyanamide at Various Rates, With and Without Propionic Acid at 250 mg/kg of Soil)

| Cyanamide Application Rate (mg/kg soil) | Number of Surviving Nematodes per 100 mL of soil | | | | | | | |
|---|---|---|---|---|---|---|---|---|
| | Deleterious Nematodes | | | | Beneficial Nematodes | | | |
| | Reniform | | Spiral | | Microbivorous | | Dorylaimida | |
| | Cyanamide Alone | With $C_2H_5CO_2H$ | Cyanamide Alone | With $C_2H_5CO_2H$ | Cyanamide Alone | With $C_2H_5CO_2H$ | Cyanamide Alone | With $C_2H_5CO_2H$ |
| 0 | 556 | 280 | 92 | 47 | 129 | 66 | 12 | 6 |
| 20 | 274 | 167 | 102 | 27 | 92 | 73 | 24 | 2 |
| 40 | 191 | 143 | 95 | 15 | 86 | 79 | 20 | 1 |
| 60 | 102 | 151 | 59 | 10 | 96 | 100 | 5 | 1 |
| 80 | 120 | 113 | 76 | 11 | 144 | 39 | 6 | 0 |
| 120 | 16 | 28 | 18 | 3 | 75 | 37 | 0 | 1 |

TABLE II

Nematicidal Activity of Cyanamid and Propionic Acid in Combination
Final Test Results: 57 Days After Treatment and 45 Days After Crop Planting
(Cyanamide at Various Rates, With and Without Propionic Acid at 250 mg/kg of Soil)

| Cyanamide Application Rate (mg/kg soil) | Number of Surviving Nematodes per 100 mL of soil | | | | | | | |
|---|---|---|---|---|---|---|---|---|
| | Deleterious Nematodes | | | | Beneficial Nematodes | | | |
| | Reniform | | Spiral | | Microbivorous | | Dorylaimida | |
| | Cyanamide Alone | With $C_2H_5CO_2H$ | Cyanamide Alone | With $C_2H_5CO_2H$ | Cyanamide Alone | With $C_2H_5CO_2H$ | Cyanamide Alone | With $C_2H_5CO_2H$ |
| 0 | 357 | 328 | 23.4 | 12.4 | 160 | 45 | 18.1 | 6 |
| 20 | 240 | 286 | 6.7 | 9.7 | 132 | 77 | 9 | 8 |
| 40 | 190 | 357 | 3.7 | 3.7 | 121 | 55 | 8 | 1 |
| 60 | 167 | 267 | 2.9 | 5.6 | 78 | 108 | 4 | 4 |

TABLE II-continued

Nematicidal Activity of Cyanamid and Propionic Acid in Combination
Final Test Results: 57 Days After Treatment and 45 Days After Crop Planting
(Cyanamide at Various Rates, With and Without Propionic Acid at 250 mg/kg of Soil)

| Cyanamide Application Rate (mg/kg soil) | Number of Surviving Nematodes per 100 mL of soil | | | | | | | |
|---|---|---|---|---|---|---|---|---|
| | Deleterious Nematodes | | | | Beneficial Nematodes | | | |
| | Reniform | | Spiral | | Microbivorous | | Dorylaimida | |
| | Cyanamide Alone | With $C_2H_5CO_2H$ | Cyanamide Alone | With $C_2H_5CO_2H$ | Cyanamide Alone | With $C_2H_5CO_2H$ | Cyanamide Alone | With $C_2H_5CO_2H$ |
| 80 | 354 | 182 | 9.8 | 4.6 | 99 | 104 | 5 | 0 |
| 120 | 95 | 65 | 4.7 | 4.4 | 52 | 117 | 0 | 0 |

TABLE III

Nematodes in the Root System: 57 Days After Treatment and 45 Days After Crop Planting
(Cyanamide at Various Rates, With and Without Propionic Acid at 250 mg/kg of Soil)

| Cyanamide Application Rate (mg/kg soil) | Number of Surviving Nematodes in Root System Per Pot | | | | | |
|---|---|---|---|---|---|---|
| | Deleterious Nematodes | | | | Microbivorous Nematodes | |
| | Reniform | | Spiral | | | |
| | Cyanamide Alone | With $C_2H_5CO_2H$ | Cyanamide Alone | With $C_2H_5CO_2H$ | Cyanamide Alone | With $C_2H_5CO_2H$ |
| 0 | 26.35 | 64.7 | 42.3 | 25.9 | 104.2 | 96 |
| 20 | 25.7 | 17.5 | 42.3 | 21 | 176.9 | 153 |
| 40 | 9.6 | 16.2 | 38.6 | 24 | 126.9 | 207 |
| 60 | 13.4 | 21.6 | 42 | 20 | 118 | 138 |
| 80 | 19.4 | 18.4 | 28 | 12 | 113 | 112 |
| 120 | 4.3 | 5.6 | 16 | 4 | 123 | 114 |

TABLE IV

Crop (Soybean) Conditions: 57 Days After Treatment and 45 Days After Crop Planting at 5 Crop Seeds/Pot
(Cyanamide at Various Rates, With and Without Propionic Acid at 250 mg/kg of Soil)

| Cyanamide Application Rate (mg/kg soil) | Number of Plants/Pot | | Shoot Height (cm) | | Fresh Shoot Weight (g) | | Root Condition Index | |
|---|---|---|---|---|---|---|---|---|
| | Cyanamide Alone | With $C_2H_5CO_2H$ | Cyanamide Alone | With $C_2H_5CO_2H$ | Cyanamide Alone | With $C_2H_5CO_2H$ | Cyanamide Alone | With $C_2H_5CO_2H$ |
| 0 | 4.3 | 3.7 | 25.4 | 26.9 | 20.6 | 19.6 | 2 | 2.1 |
| 20 | 4 | 4.6 | 26.4 | 26.4 | 21.7 | 22.2 | 1.6 | 1.3 |
| 40 | 3.9 | 4.1 | 26.5 | 26.3 | 20.5 | 22.1 | 1.4 | 1.3 |
| 60 | 4.7 | 4 | 27 | 27.6 | 25.5 | 22.6 | 1.1 | 1 |
| 80 | 4.4 | 4.6 | 27.1 | 28.5 | 24.95 | 23.6 | 1.1 | 1 |
| 120 | 4.9 | 4.3 | 28.7 | 28.8 | 29.4 | 27 | 1.3 | 1.3 |

EXAMPLE 2

This example demonstrates the herbicidal activity of hydrogen cyanamide and propionic acid in combination in pre-emergence application to soil seeded with a series of common weeds germinating in covered pots. The weeds used in these tests were grown from a standard weed seed pack of common annual and perennial weeds representing an extreme weed situation. The weeds included yellow nutsedge (*Cyperus esculentus*), crabgrass (*Digitaria sanguinalis*), pigweed (*Amaranthus* spp.), morningglory (*Ipomoea* spp.), sicklepod (*Sienna obtusifolia*) and other annual weeds. Observations of the effects on the weed population as a whole were made, and individual observations were made for yellow nutsedge, crabgrass, and sicklepod.

Figure 3:
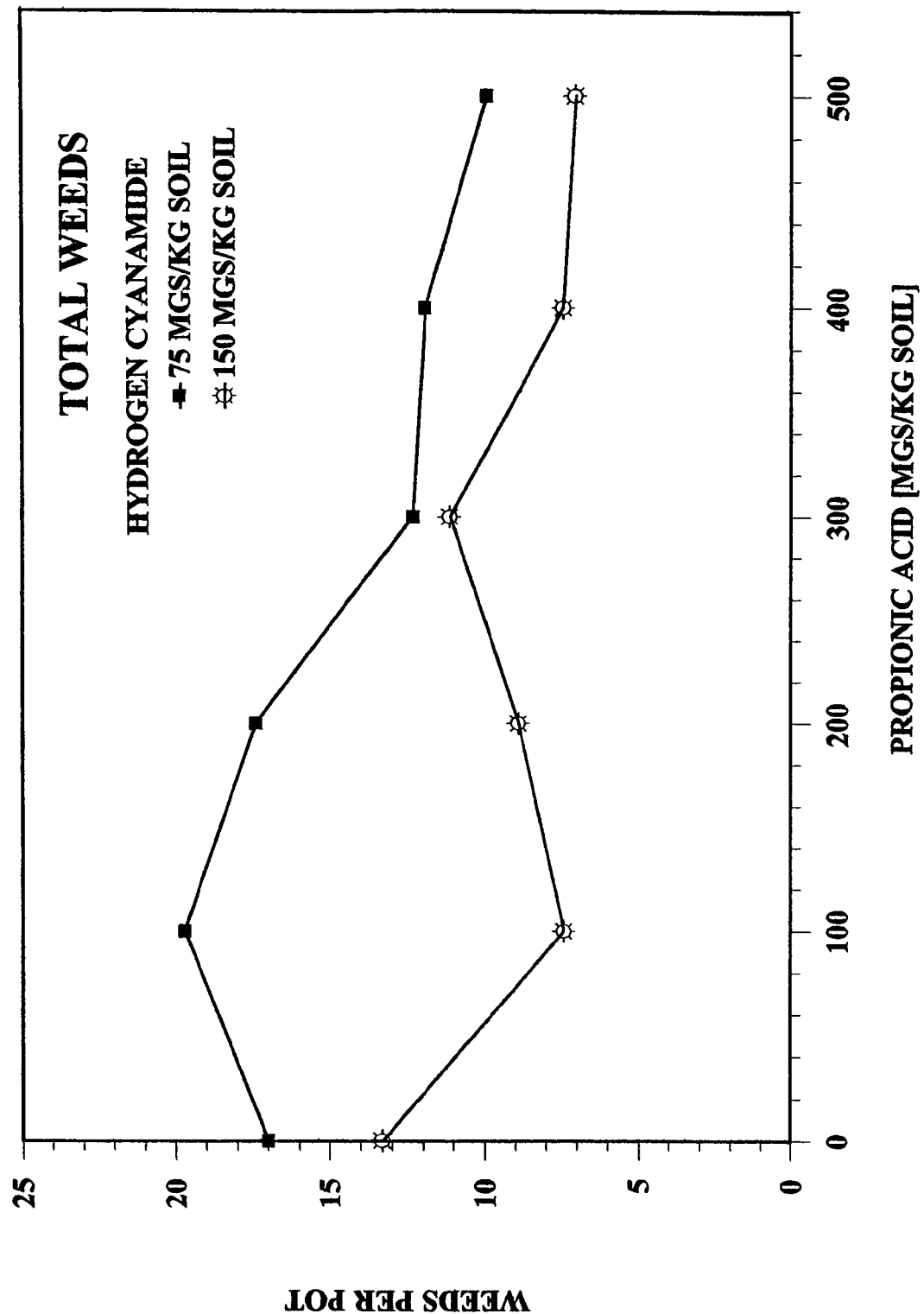
FIG. 3 is a plot of the results of tests performed in accordance with this invention, showing herbicidal activity in pre-emergence application on a collective group of common crop weeds.
Figure 4:
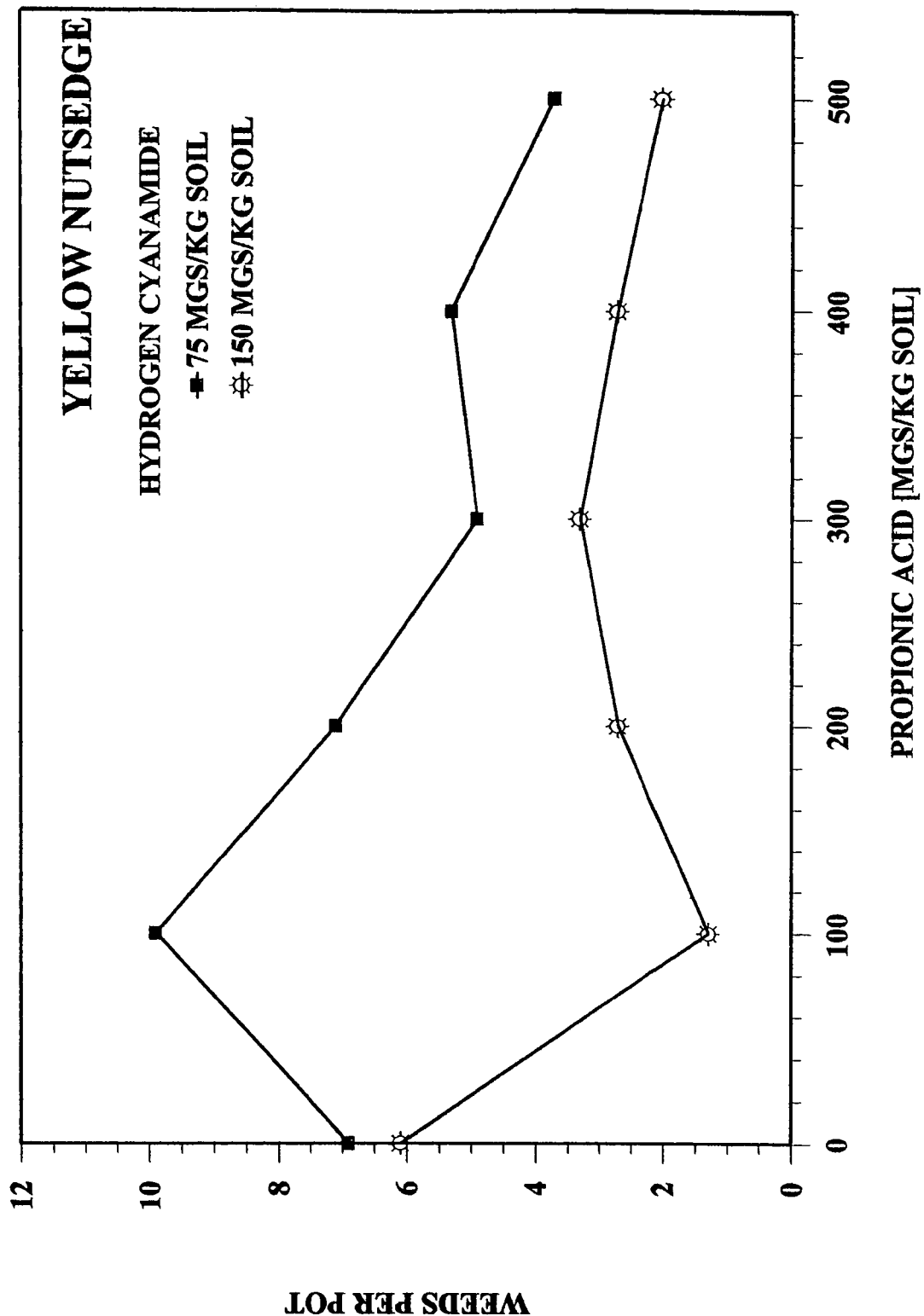
FIG. 4 is a plot of the results of tests performed in accordance with this invention, showing herbicidal activity in pre-emergence application on yellow nutsedge.
Figure 5:
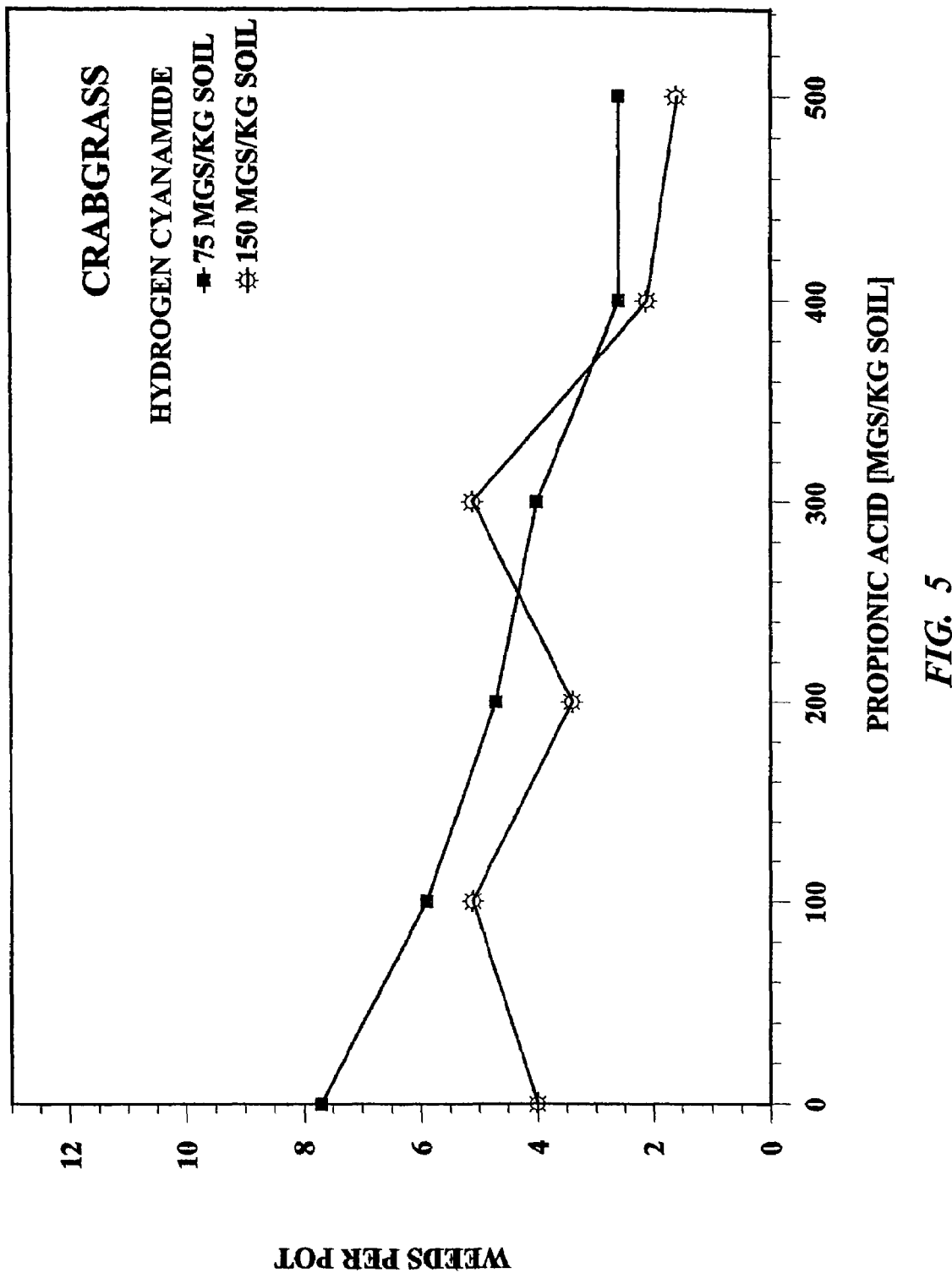
FIG. 5 is a plot of the results of tests performed in accordance with this invention, showing herbicidal activity in pre-emergence application on crabgrass.
Figure 6:
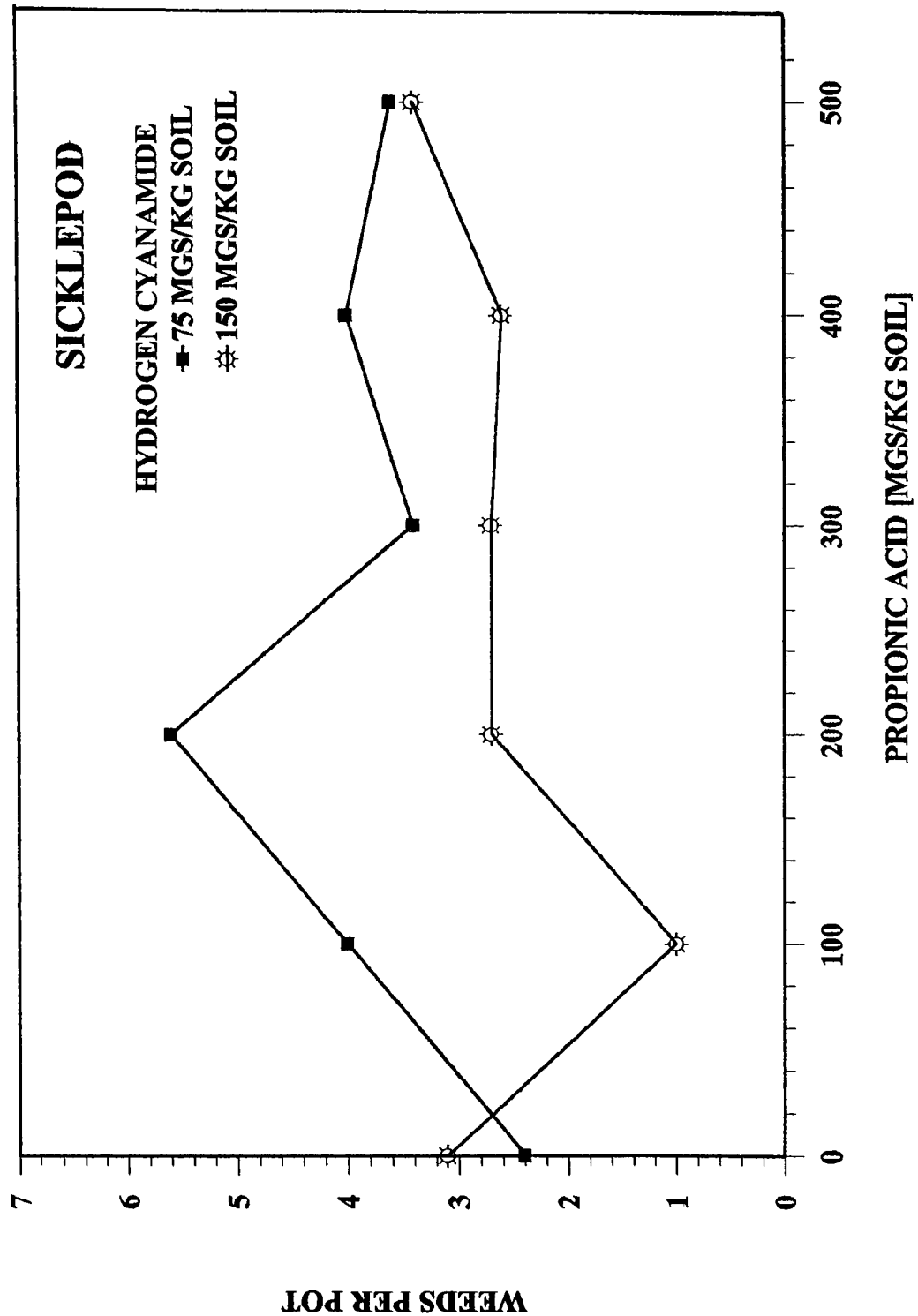
FIG. 6 is a plot of the results of tests performed in accordance with this invention, showing herbicidal activity in pre-emergence application on sicklepod.

Stock solutions of hydrogen cyanamide at 1.25% by weight and propionic acid at 5.0% by weight, both in water, were prepared, the hydrogen cyanamide from a phosphate-buffered 50% aqueous solution. The sizes of the planting pots, the amount of soil per pot, and the type of soil, were all the same as those used in Example 1. As in Example 1, the treatment chemicals were combined in various dilutions such that 100 mL of the combined dilutions contained the desired amount of each chemical for each test, and the combined dilutions were applied to the soil surface in each pot at 100 mL of combined dilution per pot. Immediately after application of the chemicals, each pot was covered by a thick (1.5 mil), clear, low-density polyethylene bag. After one week, the bags were removed and weed counts were taken from each pot at intervals of 8, 14, 20, and 27 days after application of the chemicals. Data analyses were performed in the same manner as Example 1. The results expressed in weeds per pot are listed in Table V for all weeds, Table VI for yellow nutsedge, Table VII for crabgrass, and Table VIII for sicklepod, all at various application rates for both hydrogen cyanamide and propionic acid. The results at 27 days are also plotted for all weeds in FIG. 3, yellow nutsedge in FIG. 4, crabgrass in FIG. 5, and sicklepod in FIG. 6.

The results indicate that the herbicidal activity of hydrogen cyanamide against all weed species is enhanced by propionic acid over a significant portion of the application rates used, with much of the data indicating a synergistic effect. Particularly effective results were observed when the application rate of the hydrogen cyanamide was 150 mg/kg of soil.

TABLE V

Herbicidal Activity of Cyanamide and Propionic Acid in Combination Against All Weed Species in Pre-Emergence Application in Covered Pots

| $C_2H_5CO_2H$ Application Rate | Weeds Per Pot: All Weeds | | | | | | | |
|---|---|---|---|---|---|---|---|---|
| | Cyanamide Application Rate: 75 mg/kg soil) | | | | Cyanamide Application Rate 150 mg/kg soil | | | |
| | Days After Treatment | | | | | | | |
| (mg/kg soil) | 8 | 14 | 20 | 27 | 8 | 14 | 20 | 27 |
| 0 | 2.6 | 8.7 | 15.1 | 17 | 0.6 | 4.6 | 9.9 | 13.3 |
| 100 | 6 | 13.6 | 15 | 19.7 | 0 | 1.4 | 4.9 | 7.4 |
| 200 | 3 | 10 | 12.4 | 17.4 | 0.6 | 2.9 | 5.26 | 8.9 |
| 300 | 0.6 | 5 | 9.4 | 12.3 | 0.3 | 2.7 | 6.46 | 11.1 |
| 400 | 1.6 | 6.3 | 8.9 | 11.9 | 0.1 | 3.4 | 6.1 | 7.4 |
| 500 | 0.9 | 4.1 | 9.9 | 9.9 | 0 | 3.4 | 5.9 | 7 |
| Control | 16.3 | 22.2 | 25.45 | 23.5 | 16.3 | 22.2 | 25.45 | 23.5 |

TABLE VI

Herbicidal Activity of Cyanamide and Propionic Acid in Combination Against Yellow Nutsedge in Pre-Emergence Application in Covered Pots

| $C_2H_5CO_2H$ Application Rate | Weeds Per Pot: Yellow Nutsedge | | | | | | | |
|---|---|---|---|---|---|---|---|---|
| | Cyanamide Application Rate: 75 mg/kg soil) | | | | Cyanamide Application Rate 150 mg/kg soil | | | |
| | Days After Treatment | | | | | | | |
| (mg/kg soil) | 8 | 14 | 20 | 27 | 8 | 14 | 20 | 27 |
| 0 | 1.4 | 3.6 | 4.6 | 6.9 | 0.1 | 2.4 | 3.4 | 6.1 |
| 100 | 3.1 | 4.4 | 5.3 | 9.9 | 0 | 0.4 | 1 | 1.3 |
| 200 | 1 | 2.9 | 4.3 | 7.1 | 0.3 | 1.1 | 1.7 | 2.7 |
| 300 | 0.6 | 2.4 | 3.3 | 4.9 | 0.3 | 1 | 1.8 | 3.3 |
| 400 | 0.84 | 2.2 | 3.3 | 5.3 | 0.1 | 1.4 | 1.9 | 2.7 |
| 500 | 0.9 | 1.9 | 2.9 | 3.7 | 0 | 1.1 | 1.4 | 2 |
| Control | 3.2 | 4.5 | 5.2 | 5.7 | 3.2 | 4.5 | 5.2 | 5.7 |

TABLE VII

Herbicidal Activity of Cyanamide and Propionic Acid in Combination Against Crabgrass in Pre-Emergence Application in Covered Pots

| $C_2H_5CO_2H$ Application Rate | Weeds Per Pot: Crabgrass | | | | | | | |
|---|---|---|---|---|---|---|---|---|
| | Cyanamide Application Rate: 75 mg/kg soil) | | | | Cyanamide Application Rate 150 mg/kg soil | | | |
| | Days After Treatment | | | | | | | |
| (mg/kg soil) | 8 | 14 | 20 | 27 | 8 | 14 | 20 | 27 |
| 0 | 0 | 3.3 | 8.6 | 7.7 | 0 | 0 | 3.7 | 4 |
| 100 | 0.4 | 5 | 5.6 | 5.9 | 0 | 0.1 | 2.4 | 5.1 |
| 200 | 0.3 | 3.3 | 4.4 | 4.7 | 0 | 0 | 3.1 | 3.4 |
| 300 | 0 | 1.3 | 3 | 4 | 0 | 0.1 | 3.3 | 5.1 |
| 400 | 0 | 0.9 | 2.4 | 2.6 | 0 | 0.1 | 2.4 | 2.1 |
| 500 | 0 | 0.4 | 2.9 | 2.6 | 0 | 0.7 | 1.4 | 1.6 |
| Control | 6.7 | 14.1 | 15.85 | 12.4 | 6.7 | 14.1 | 15.85 | 12.4 |

TABLE VIII

Herbicidal Activity of Cyanamide and Propionic Acid in Combination Against Sicklepod in Pre-Emergence Application in Covered Pots

| $C_2H_5CO_2H$ Application Rate | Weeds Per Pot: Sicklepod | | | | | | | |
|---|---|---|---|---|---|---|---|---|
| | Cyanamide Application Rate: 75 mg/kg soil) | | | | Cyanamide Application Rate 150 mg/kg soil | | | |
| | Days After Treatment | | | | | | | |
| (mg/kg soil) | 8 | 14 | 20 | 27 | 8 | 14 | 20 | 27 |
| 0 | 1 | 1.9 | 2 | 2.4 | 0.4 | 2.1 | 2.7 | 3.1 |
| 100 | 2.4 | 4.1 | 4.1 | 4 | 0 | 0.9 | 1.4 | 1 |
| 200 | 1.7 | 3.9 | 4.4 | 5.6 | 0 | 1.7 | 2 | 2.7 |
| 300 | 0 | 1.3 | 3.1 | 3.4 | 0.3 | 1.6 | 1.7 | 2.7 |
| 400 | 0 | 1.8 | 3.1 | 4 | 0 | 1.9 | 1.9 | 2.6 |
| 500 | 0 | 1.9 | 4.1 | 3.6 | 0 | 1.7 | 2 | 3.4 |
| Control | 3.9 | 4.3 | 4.1 | 4.6 | 3.9 | 4.3 | 4.1 | 4.6 |

EXAMPLE 3

This example demonstrates the herbicidal activity of hydrogen cyanamide and propionic acid in combination in application to soil seeded with the same weed species used in Example 2. The procedures in this example differed from those of Example 2, however, by the use of hydrogen cyanamide crystals free of phosphate ion to prepare the aqueous hydrogen cyanamide solution, by the use of post-emergence application, and by the omission of any covering of the pots during any part of the test. Observations were made for total weed growth, and individual observations were also made for yellow nutsedge, crabgrass, sicklepod, and morningglory.

Figure 7:
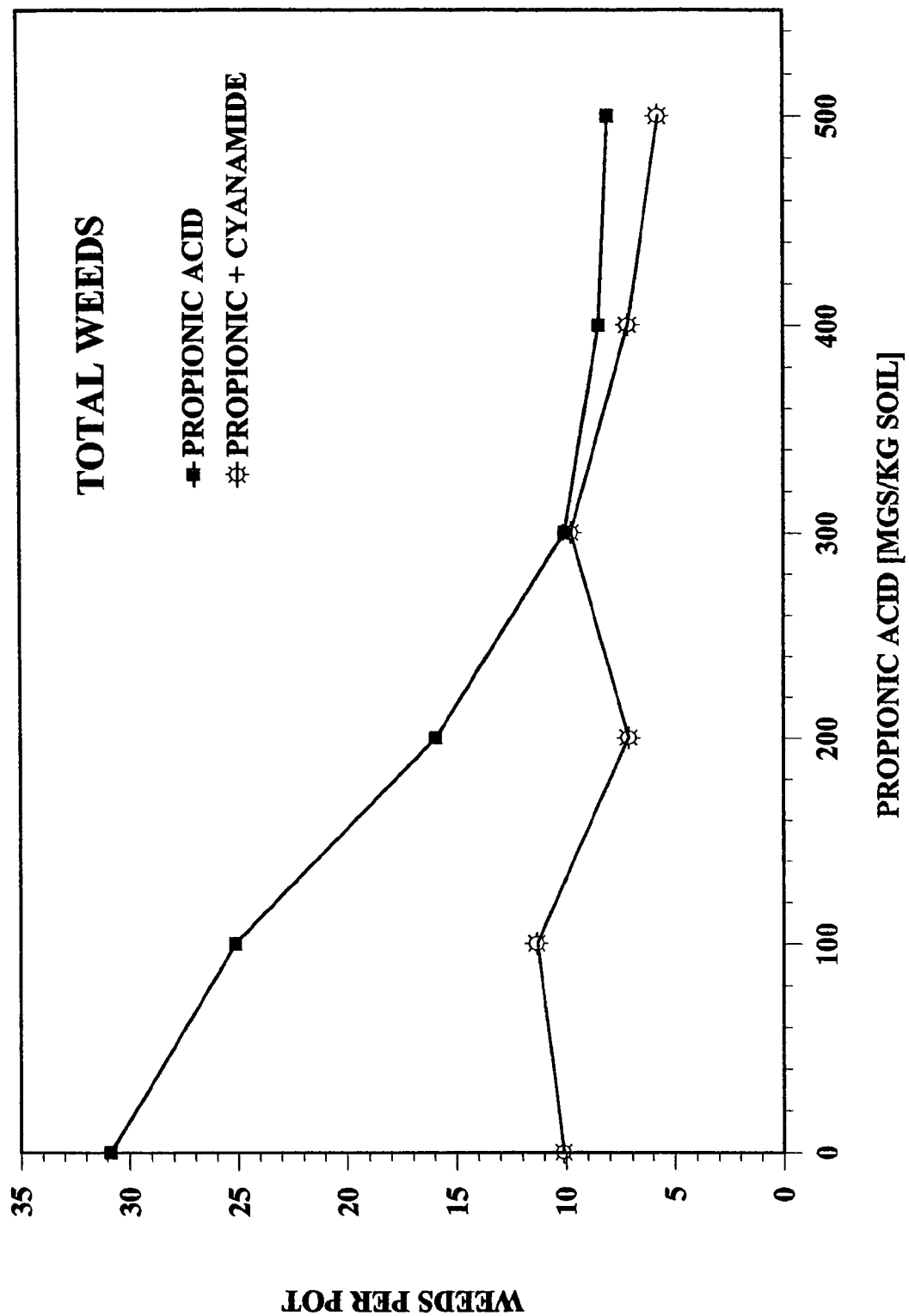
FIG. 7 is a plot of the results of tests performed in accordance with this invention, showing herbicidal activity in post-emergence application on a collective group of common crop weeds.

Stock solutions of hydrogen cyanamide at 1.25% by weight and propionic acid at 5.0% by weight, both in water, were prepared as before, except that the hydrogen cyanamide solution, as noted above, was prepared by dissolving hydrogen cyanamide crystals in water in the absence of phosphate ion. The sizes of the planting pots, the amount of soil per pot, and the type of soil, were all the same as those used in Examples 1 and 2. The treatment chemicals were combined in various dilutions such that 100 mL of the combined dilutions contained the desired amount of each chemical for each test. The weeds were allowed to grow for three weeks before the treatment chemicals were applied. The treatment chemicals were then applied to the soil surface in each pot at 100 mL of combined dilution per pot, with the pots left uncovered. Weed counts were then taken at intervals of 8, 14, 20, and 27 days after application of the chemicals. Data analyses were performed in the same manner as Examples 1 and 2. Table IX lists the results in weeds per pot for all weeds, Table X for yellow nutsedge, Table XI for crabgrass, Table XII for sicklepod, and Table XIII for morningglory, all both with propionic acid alone at various application rates and with propionic acid at the same application rates but in combination with hydrogen cyanamide at 125 mg/kg of soil. The results at 20 days are also plotted for all weeds in FIG. 7.

These test results indicate that the application rate of hydrogen cyanamide (125 mg/kg of soil) was sufficient to control the weeds very effectively when applied alone, with less than ten total weeds per pot at all intervals, including about one or fewer crabgrass weeds per pot, about one or fewer sicklepod weeds per pot, about three or fewer morningglory weeds per pot, and about six or fewer yellow nutsedge weeds per pot. Propionic acid demonstrated herbicidal activity on its own, but most significantly, the propionic acid did not significantly impair the herbicidal activity of the hydrogen cyanamide in any of the tests. This confirms that the combination of hydrogen cyanamide and propionic acid can be used for effective nematode and weed control (considering these results in combination with those of Example 1) with enhanced nematicidal activity and no loss in herbicidal activity.

TABLE IX

Herbicidal Activity of Cyanamide (Phosphate-Free) and Propionic Acid in Combination Against All Weed Species in Post-Emergence Application in Uncovered Pots

| $C_2H_5CO_2H$ Application Rate (mg/kg soil) | Weeds Per Pot: All Weeds | | | | | |
|---|---|---|---|---|---|---|
| | Without Cyanamide | | | With 150 mg Cyanamide/kg soil | | |
| | Days After Treatment | | | | | |
| | 6 | 13 | 20 | 6 | 13 | 20 |
| 0 | 26.5 | 27.95 | 30.85 | 6.3 | 7.7 | 10.1 |
| 100 | 22.4 | 24.4 | 25.1 | 5.6 | 10.9 | 11.3 |
| 200 | 12.6 | 14.9 | 15.9 | 2.6 | 6.1 | 7.1 |
| 300 | 5.7 | 8.6 | 10 | 3.3 | 7.1 | 9.7 |
| 400 | 4 | 7.6 | 8.4 | 1.1 | 4.4 | 7.1 |
| 500 | 3.4 | 6.7 | 8 | 2 | 5.7 | 5.7 |

TABLE X

Herbicidal Activity of Cyanamide (Phosphate-Free) and Propionic Acid in Combination Against Yellow Nutsedge in Post-Emergence Application in Uncovered Pots

| $C_2H_5CO_2H$ Application Rate (mg/kg soil) | Weeds Per Pot: Yellow Nutsedge | | | | | |
|---|---|---|---|---|---|---|
| | Without Cyanamide | | | With 150 mg Cyanamide/kg soil | | |
| | Days After Treatment | | | | | |
| | 6 | 13 | 20 | 6 | 13 | 20 |
| 0 | 3.2 | 3.4 | 3.9 | 2.4 | 4.6 | 6 |
| 100 | 2.4 | 3 | 3.1 | 2.6 | 5.4 | 6.1 |
| 200 | 4 | 4.9 | 5.4 | 1.7 | 2.6 | 5.2 |
| 300 | 1.9 | 3.3 | 4.7 | 2.4 | 2.4 | 5.9 |
| 400 | 3 | 4.7 | 5.3 | 1 | 2.1 | 4.1 |
| 500 | 2.1 | 3.9 | 4.1 | 1.1 | 1.7 | 2.3 |

TABLE XI

Herbicidal Activity of Cyanamide (Phosphate-Free) and Propionic Acid in Combination Against Crabgrass in Post-Emergence Application in Uncovered Pots

| $C_2H_5CO_2H$ Application Rate (mg/kg soil) | Weeds Per Pot: Crabgrass | | | | | |
|---|---|---|---|---|---|---|
| | Without Cyanamide | | | With 150 mg Cyanamide/kg soil | | |
| | Days After Treatment | | | | | |
| | 6 | 13 | 20 | 6 | 13 | 20 |
| 0 | 11.7 | 12.6 | 14.85 | 0 | 0.4 | 0.3 |
| 100 | 9.9 | 10.6 | 11.6 | 0.4 | 1.6 | 1.9 |
| 200 | 5.1 | 5.4 | 6 | 0.3 | 1.7 | 1.3 |
| 300 | 3 | 3.9 | 3.4 | 0.3 | 1.1 | 1.6 |
| 400 | 0.6 | 1.3 | 1.3 | 0 | 0.9 | 0.9 |
| 500 | 0.6 | 0.7 | 1.6 | 0 | 1.3 | 1.1 |

TABLE XII

Herbicidal Activity of Cyanamide (Phosphate-Free) and Propionic Acid in Combination Against Sicklepod in Post-Emergence Application in Uncovered Pots

| $C_2H_5CO_2H$ Application Rate (mg/kg soil) | Weeds Per Pot: Sicklepod | | | | | |
|---|---|---|---|---|---|---|
| | Without Cyanamide | | | With 150 mg Cyanamide/kg soil | | |
| | Days After Treatment | | | | | |
| | 6 | 13 | 20 | 6 | 13 | 20 |
| 0 | 3.1 | 3.5 | 3.6 | 0.6 | 1.4 | 1 |
| 100 | 3.1 | 3.6 | 3.1 | 0.6 | 1.7 | 1.3 |
| 200 | 1.3 | 2.4 | 2.3 | 0.4 | 1.7 | 2.4 |
| 300 | 0.9 | 1.4 | 1.9 | 0.6 | 1.9 | 2.3 |
| 400 | 0.4 | 1.6 | 1.9 | 0.1 | 1.4 | 2.1 |
| 500 | 0.7 | 2 | 2.1 | 0.9 | 2.5 | 2.9 |

TABLE XIII

Herbicidal Activity of Cyanamide (Phosphate-Free) and Propionic Acid in Combination Against Morningglory in Post-Emergence Application in Uncovered Pots

| $C_2H_5CO_2H$ Application Rate (mg/kg soil) | Weeds Per Pot: Morningglory | | | | | |
|---|---|---|---|---|---|---|
| | Without Cyanamide | | | With 150 mg Cyanamide/kg soil | | |
| | Days After Treatment | | | | | |
| | 6 | 13 | 20 | 6 | 13 | 20 |
| 0 | 8.5 | 8.5 | 8.5 | 3.3 | 2.7 | 2.9 |
| 100 | 7 | 7.3 | 7.3 | 2 | 2.1 | 2 |
| 200 | 2.1 | 2.1 | 2.1 | 0.1 | 0.1 | 0.3 |
| 300 | 0 | 0 | 0 | 0 | 0 | 0 |
| 400 | 0 | 0 | 0 | 0 | 0 | 0 |
| 500 | 0 | 0 | 0 | 0 | 0 | 0 |

The foregoing is offered primarily for purposes of illustration. Persons skilled in agricultural chemistry will recognize that further modifications, additions, and substitutions that still embody the essence of the invention in both its spirit and scope, as expressed in the claims.

What is claimed is:

1. A composition for controlling organisms in soil that are deleterious to crop growth, said composition comprising amounts of hydrogen cyanamide and a $C_1$-$C_4$ straight-chain, water-soluble monocarboxylic acid that is synergistically effective to control such organisms when the composition is applied to soil, at a monocarboxylic acid:hydrogen cyanamide weight ratio of from about 1:1 to about 20:1.

2. The composition of claim 1 wherein the weight ratio is from about 2:1 to about 10:1.

3. The composition of claim 1 wherein the concentration of hydrogen cyanamide in said aqueous solution is from about 0.1% to about 10% by weight, and the concentration of said monocarboxylic acid in said aqueous solution is from about 0.1% to about 20% by weight.

4. The composition of claim 1 wherein the concentration of hydrogen cyanamide in said aqueous solution is from about 0.3% to about 3% by weight, and the concentration of said monocarboxylic acid in said aqueous solution is from about 1% to about 10% by weight.

5. The composition of claim 1 wherein said composition comprises no more than a trace amount of phosphate ion.

6. The composition of claim 1 wherein said composition is devoid of phosphate ion.

7. The composition of claim 1 wherein said organisms are (i) nematode species that are deleterious to crop growth and (ii) undesirable vegetation.

* * * * *